(12) United States Patent
Ferree

(10) Patent No.: US 8,679,180 B2
(45) Date of Patent: *Mar. 25, 2014

(54) DEVICES USED TO TREAT DISC HERNIATION AND ATTACHMENT MECHANISMS THEREFORE

(75) Inventor: Bret A. Ferree, Cincinnati, OH (US)

(73) Assignee: Anova Corporation, Summit, NJ (US)

( * ) Notice: Subject to any disclaimer, the term of this patent is extended or adjusted under 35 U.S.C. 154(b) by 643 days.

This patent is subject to a terminal disclaimer.

(21) Appl. No.: 12/121,498

(22) Filed: May 15, 2008

(65) Prior Publication Data

US 2008/0221686 A1    Sep. 11, 2008

Related U.S. Application Data

(63) Continuation of application No. 10/185,284, filed on Jun. 26, 2002, now abandoned, which is a continuation-in-part of application No. 09/415,382, filed on Oct. 18, 1999, now Pat. No. 6,419,704.

(51) Int. Cl.
*A61F 2/44* (2006.01)
*A61B 17/70* (2006.01)
*A61B 17/88* (2006.01)

(52) U.S. Cl.
USPC ........................................ 623/17.11; 606/279

(58) Field of Classification Search
USPC ...................... 623/17.11, 17.12, 17.13, 17.16; 606/246, 279

See application file for complete search history.

(56) References Cited

U.S. PATENT DOCUMENTS

| | | | |
|---|---|---|---|
| 4,413,359 A | 11/1983 | Akiyama | |
| 4,512,338 A | 4/1985 | Balko | |
| 4,599,086 A | 7/1986 | Doty | |
| 4,636,217 A | 1/1987 | Ogilvie | |
| 4,663,358 A | 5/1987 | Hyon | |
| 4,743,256 A | 5/1988 | Brantigan | |
| 4,772,287 A | 9/1988 | Ray | |
| 4,834,757 A | 5/1989 | Brantigan | |
| 4,904,260 A | 2/1990 | Ray | |
| 4,932,969 A | 6/1990 | Frey | |
| 4,950,258 A | 8/1990 | Kawai | |
| 5,015,255 A | 5/1991 | Kuslich | |
| 5,047,055 A | 9/1991 | Bao | |
| 5,059,193 A | 10/1991 | Kuslich | |
| 5,100,422 A | 3/1992 | Berguer | |
| 5,123,926 A | 6/1992 | Pisharodi | |
| 5,147,374 A | 9/1992 | Fernandez | |
| 5,171,278 A | 12/1992 | Pisharodi | |
| 5,192,326 A | 3/1993 | Bao | |
| 5,258,043 A | 11/1993 | Stone | |

(Continued)

*Primary Examiner* — Pedro Philogene
*Assistant Examiner* — David Comstock
(74) *Attorney, Agent, or Firm* — Pandiscio & Pandiscio

(57) ABSTRACT

A method for retaining an intra-discal material within an annulus fibrosis having a posterior annulus, an inside surface, and an opening is described. The opening has a lateral and a vertical dimension. A retention device that includes a shape memory alloy is inserted through the opening in the annulus fibrosis. The length dimension of the device is longer than the lateral dimension of the opening and the width dimension of the device is longer than the vertical dimension of the opening in the annulus fibrosis. The retention device is positioned against the posterior annulus to rest against annulus fibrosis tissues adjacent the opening on the inside surface of the annulus fibrosis such that both a portion of the length dimension and a portion of the width dimension rests against annulus fibrosis tissues adjacent the opening. The retention device prevents the escape of intra-discal material through the opening.

28 Claims, 16 Drawing Sheets

(56) References Cited

U.S. PATENT DOCUMENTS

| | | | |
|---|---|---|---|
| 5,304,194 | A | 4/1994 | Chee |
| 5,342,394 | A | 8/1994 | Matsuno |
| 5,370,660 | A | 12/1994 | Weinstein |
| 5,390,683 | A | 2/1995 | Pisharodi |
| 5,425,772 | A | 6/1995 | Brantigan |
| 5,496,318 | A | 3/1996 | Howland |
| 5,540,715 | A | 7/1996 | Katsaros |
| 5,545,229 | A | 8/1996 | Parsons |
| 5,562,736 | A | 10/1996 | Ray |
| 5,571,189 | A | 11/1996 | Kuslich |
| 5,578,034 | A | 11/1996 | Estes |
| 5,645,597 | A | 7/1997 | Krapiva |
| 5,674,296 | A | 10/1997 | Bryan |
| 5,681,310 | A | 10/1997 | Yuan |
| 5,716,416 | A | 2/1998 | Lin |
| 5,800,549 | A | 9/1998 | Bao |
| 5,800,550 | A | 9/1998 | Sertich |
| 5,824,093 | A | 10/1998 | Ray |
| 5,827,328 | A | 10/1998 | Buttermann |
| 5,865,845 | A | 2/1999 | Thalgott |
| 5,879,366 | A | 3/1999 | Shaw |
| 5,916,225 | A | 6/1999 | Kugel |
| 5,931,838 | A | 8/1999 | Vito |
| 5,976,174 | A | 11/1999 | Ruiz |
| 5,976,186 | A | 11/1999 | Bao |
| 6,007,570 | A | 12/1999 | Sharkey |
| 6,024,754 | A | 2/2000 | Engelson |
| 6,039,761 | A | 3/2000 | Li |
| 6,039,762 | A | 3/2000 | McKay |
| 6,066,175 | A | 5/2000 | Henderson |
| 6,095,149 | A | 8/2000 | Sharkey |
| 6,132,465 | A | 10/2000 | Ray |
| 6,143,032 | A | 11/2000 | Schafer |
| 6,193,757 | B1 | 2/2001 | Foley |
| 6,206,923 | B1 | 3/2001 | Boyd |
| 6,224,602 | B1 | 5/2001 | Hayes |
| 6,224,630 | B1 | 5/2001 | Bao |
| 6,235,034 | B1 | 5/2001 | Bray |
| 6,264,695 | B1 | 7/2001 | Stoy |
| 6,425,919 | B1 | 7/2002 | Lambrecht |
| 6,488,710 | B2 | 12/2002 | Besselink |
| 6,613,089 | B1 | 9/2003 | Estes |
| 6,656,178 | B1 | 12/2003 | Veldhuizen et al. |
| 6,660,037 | B1 | 12/2003 | Husson |
| 6,712,853 | B2 | 3/2004 | Kuslich |
| 6,733,531 | B1 | 5/2004 | Trieu |
| 2002/0077701 | A1* | 6/2002 | Kuslich ............ 623/17.12 |

* cited by examiner

POSTERIOR

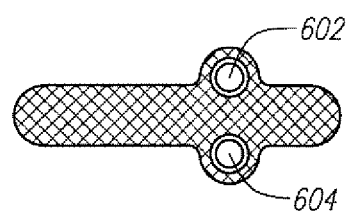 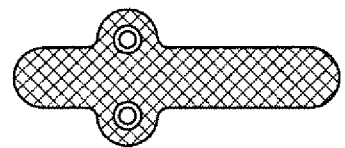
FIG. 6A  FIG. 6B
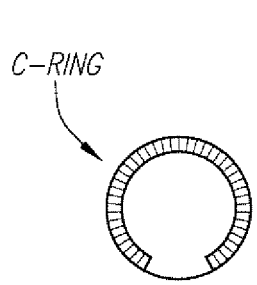 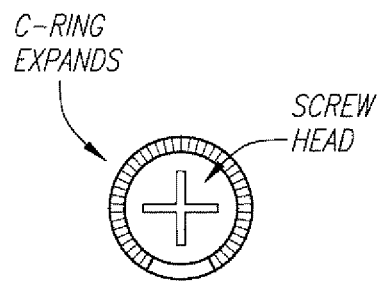 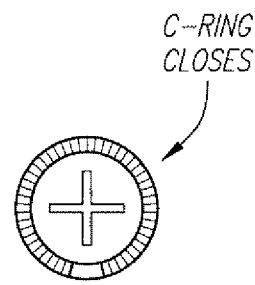
FIG. 7A  FIG. 7B  FIG. 7C

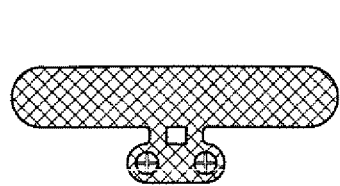
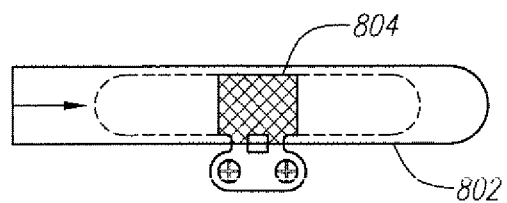
FIG. 8A    FIG. 8B
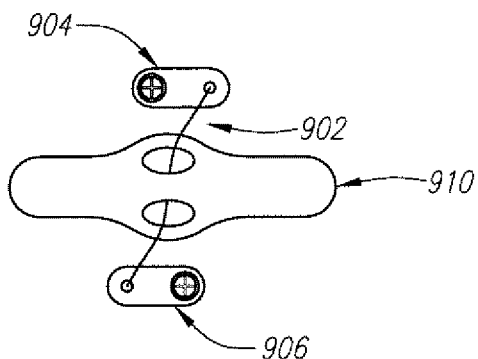
FIG. 9A
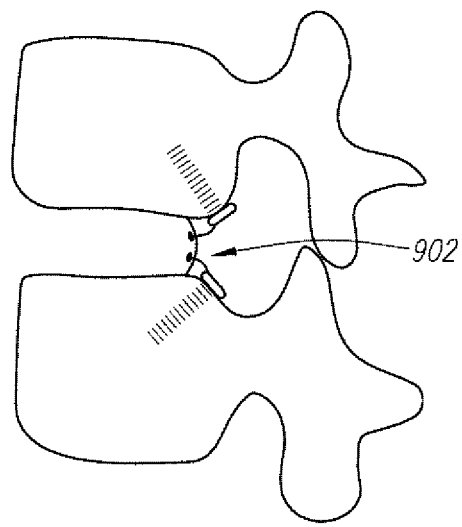
FIG. 9B

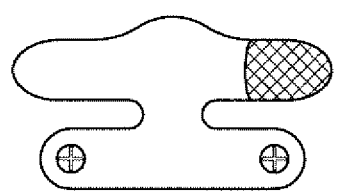
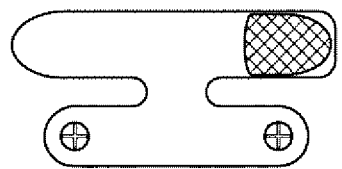
FIG. 10A          FIG. 10B
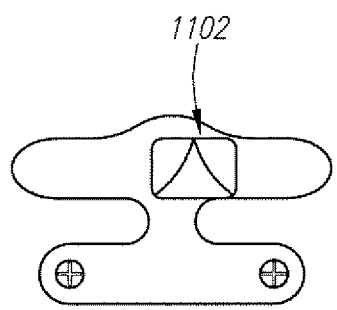
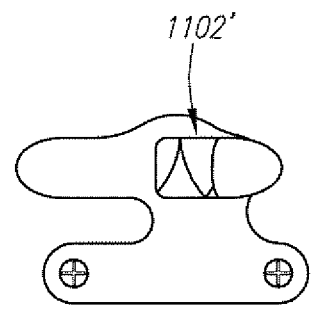
FIG. 11A          FIG. 11B

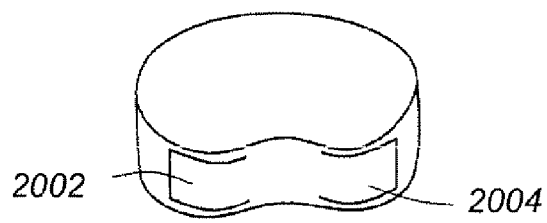
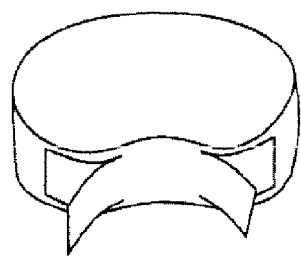
*Fig - 20A*  *Fig - 20B*
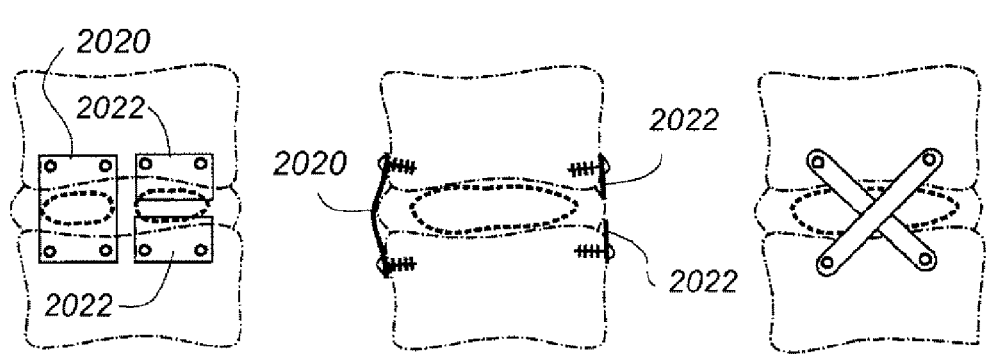
*Fig - 20C*  *Fig - 20D*  *Fig - 20E*
*Fig - 20F*  *Fig - 20G*  *Fig - 20H*

DEVICES USED TO TREAT DISC HERNIATION AND ATTACHMENT MECHANISMS THEREFORE

REFERENCE TO RELATED APPLICATIONS

This application is a continuation of U.S. application Ser. No. 10/185,284, filed Jun. 26, 2002, now abandoned, which is a continuation-in-part of U.S. application Ser. No. 09/415,382, filed Oct. 8, 1999, now U.S. Pat. No. 6,419,704. This application is related to U.S. patent application Ser. Nos. 10/120,763, filed Apr. 11, 2002; 09/807,820, filed Apr. 19, 2001, now abandoned. The entire contents of each of the above-referenced applications are incorporated herein by reference in their entirety.

FIELD OF THE INVENTION

This invention relates generally to devices used to treat disc herniation and, in particular, to attachment methods and apparatus therefore.

BACKGROUND OF THE INVENTION

Several hundred thousand patients undergo disc operations each year. Approximately five percent of these patients will suffer recurrent disc herniation, which results from a void or defect which remains in the outer layer (annulus fibrosis) of the disc after surgery involving partial discectomy.

Reference is made to FIG. 1A, an axial cross-section of a normal disc, including the "safe zones." The nucleus pulposus 102 is entirely surrounded by the annulus fibrosis 104 in the case of healthy anatomy. Also shown in this cross section is the relative location of the nerves 106. FIG. 1B illustrates the case of the herniated disc, wherein a portion of the nucleus pulposus has ruptured through a defect in the annulus fibrosis, resulting in a pinched nerve 110. This results in pain and further complications, in many cases.

FIG. 1C illustrates the post-operative anatomy following partial discectomy, wherein a space 120 remains adjacent a hole or defect in the annulus fibrosis following removal of the disc material. The hole 122 acts as a pathway for additional material to protrude into the nerve, resulting in the recurrence of the herniation. Since thousands of patients each year require surgery to treat this condition, with substantial implications in terms of the cost of medical treatment and human suffering, any solution to this problem would welcomed by the medical community.

As disclosed and described in the related applications referenced above and incorporated herein by reference, devices used to prevent recurrent disc herniations may be attached in numerous ways, depending upon the extent of the defect, overall patient physiology, and other considerations. For example, such devices may attach to the vertebral endplates, to the annulus fibrosis, to the nucleous pulposus, to the pedicle facet, or other posterior aspect of the vertebrae. Under these more generalized approaches, numerous other more targeted procedures may be used, particularly with respect to annulus fibrosis attachment. For example, devices may be attached to the inner portion of the annulus, including the inner surface, or to the outer surface. With respect to external attachment, positioning typically considers the "safe zone" so as to avoid the great vessels anteriorally, and the nerve or spinal posteriorally.

Given the great variance in defect type, as well as the variability in anatomical structure, particularly at the different vertebral levels, additional methods and apparatus used to maintain devices for preventing recurrent disc herniation are always welcome, particularly if such components, instruments and procedures lend additional stability or longevity.

SUMMARY OF THE INVENTION

This invention resides in apparatus for preventing the escape of natural, artificial, or therapeutic material through a defect in the annulus fibrosis, with particular emphasis on attachment mechanisms for such apparatus. The preferred embodiment resides a device having height and lateral extensions, the width of the lateral extensions being substantially greater than the width of the defect in the annulus, such that when the device is introduced into the disc through the defect, the extensions overlap with the annulus fibrosis on both side of the defect from the inside, thereby preventing the escape of the natural, artificial, or therapeutic material.

In one preferred embodiment, the device is in the form of an elongate band. In an alternative embodiment, the device is in the form of a plate having upper or lower extensions for respective fastening to upper or lower vertebra. The extensions are preferably fastened with screws, with the apparatus further including an anti-backout mechanism in the form of a C-ring positioned around each screw or a mobile link member from the plate to the screw.

The lateral extensions may be integral to the device or, alternatively, may be separate and outwardly biased, as with springs. The apparatus may further include an intradiscal ring to which the device attaches. The intradiscal ring may additionally includes one or more anti-rotation projections. As yet a further option, the device may be hinged, and may include mesh, teeth, or other material to further prevent the escape of the natural, artificial, or therapeutic material.

BRIEF DESCRIPTION OF THE DRAWINGS

FIG. 6A is a detailed view of disc herniation prevention plate according to the invention;

FIG. 6B is a detailed drawing of an alternative plate;

FIG. 7A is a drawing of a screw hole illustrating the use of a C-ring to prevent backout;

FIG. 7B shows the structure of FIG. 7A with the screw progressing past the C-ring;

FIG. 7C shows the screw passing through the ring, thus locking the structure in position;

FIG. 5A is a drawing of a further alternative herniation prevention plate according to the invention;

FIG. 8B illustrates the use of the plate 8A in position within the disc;

FIG. 9A illustrates an alternative mechanism to prevent screw backout;

FIG. 9B illustrates the components of FIG. 9A from a lateral perspective;

FIG. 10A is a drawing of a plate including a spring-biased extension in an extended state;

FIG. 10B illustrates the plate of FIG. 10A in a contracted state;

FIG. 11A is a cut-away view of the device in the state of FIG. 10A;

FIG. 11B is a cut-away view of the device of FIG. 10B, illustrating the spring being compressed;

FIG. 20A is an oblique representation of the way in which one or more flaps may be used to insert a prosthesis into a retainer according to the invention;

FIG. 20B is a drawing of the arrangement of FIG. 20A, but with the annular flap opened;

FIG. 20C is a drawing which illustrates the alternative use of a band to close off one or more annular flaps used to introduce an intravertebral disc replacement according to the invention;

FIG. 20D which is a drawing which furthers the configuration shown in FIG. 20C, wherein a second intervertebral disc replacement is being introduced;

FIG. 20E is a drawing which subsequent to that of FIG. 20D, wherein the band is used to close off a pair of annular flaps;

FIG. 20F is a drawing which shows how a flexible patch or retaining pieces may be used to close off a pair of annular flaps according to the invention;

FIG. 20G which shows the flexible material and retaining pieces from a side-view perspective; and FIG. 20H illustrates an alternative use of crisscross bands for use in annular flap closure.

DETAILED DESCRIPTION OF THE INVENTION

As discussed above, this invention resides in various alternative components and procedures used to treat disc herniation and recurrent disc herniation. Depending upon the precise mechanism and procedural protocol, the devices may be introduced anteriorally, posteriorally, percutaneously or laproscopically.

FIGS. 3 and 4 refer an to embodiment of the invention wherein a band is placed around the inside of the disc. This may be placed percutaneously or endoscopically utilizing steerable catheters, spinal endoscopes, and other endoscopic instruments currently in use by surgeons. Fluoroscopic guidance may advantageously be used. A single wire, band or other structure, which may or may not include a shape-memory material, is introduced into the disc space. Depending upon the circumstances, a wider band may be slid over a previously introduced smaller wire.

Minimally invasive procedures of this kind may be used on patients whose herniation has healed naturally. The procedure may also be used on patients with bulging discs, or whoever has a relatively high risk of suffering recurrent herniation. Unlike larger devices, these embodiments do not require a large incision through the annulus, as they may be inserted through a puncture just large enough to insert the band. Indeed, the fibers of the annulus may be bluntly separated as opposed to being cut.

Figure 1A:
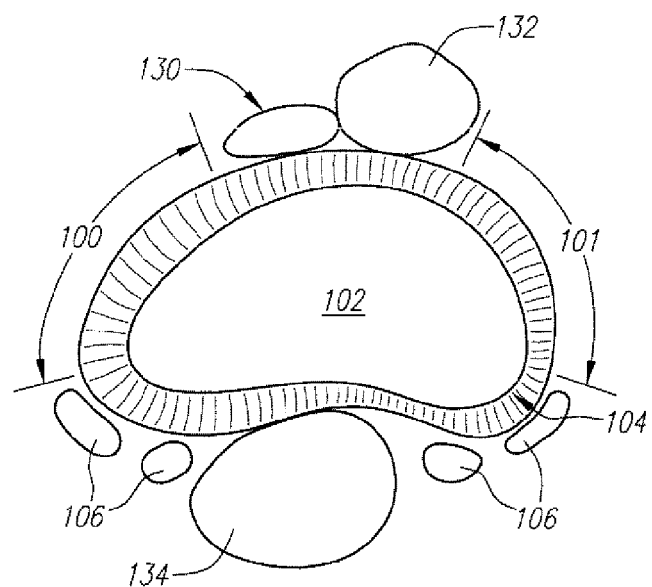
FIG. 1A is an axial cross-section of a disc and surrounding structures, illustrating the "safe zones"
Figures 1B, 1C:
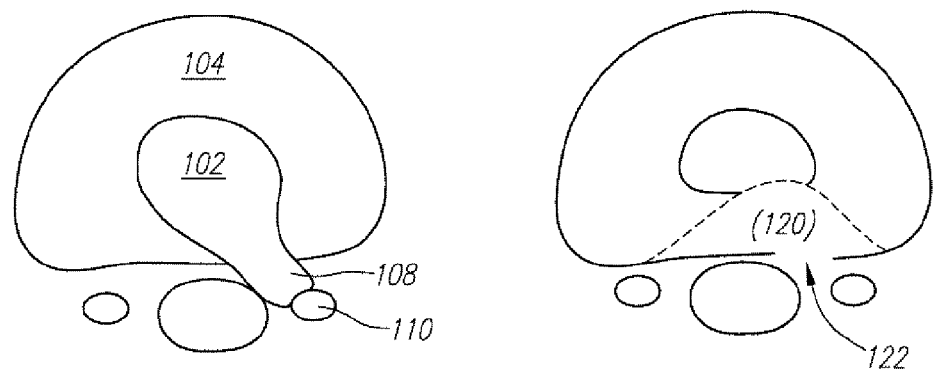
FIG. 1B illustrates the case of the herniated disc, wherein a portion of the nucleus pulposus has ruptured through a defect in the annulus fibrosis, resulting in a pinched nerve.
FIG. 1C illustrates the post-operative anatomy following partial discectomy, wherein a space remains adjacent a hole or defect in the annulus fibrosis following removal of the disc material.
Figure 2:
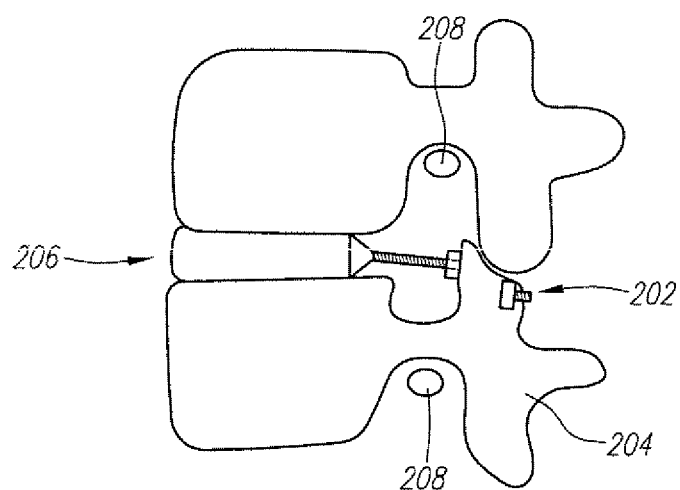
FIG. 2 is a lateral view of the spine, showing the way in which a device may be attached to the superior facet of an inferior vertebra to maintain a posterior herniation.
Figure 3A:
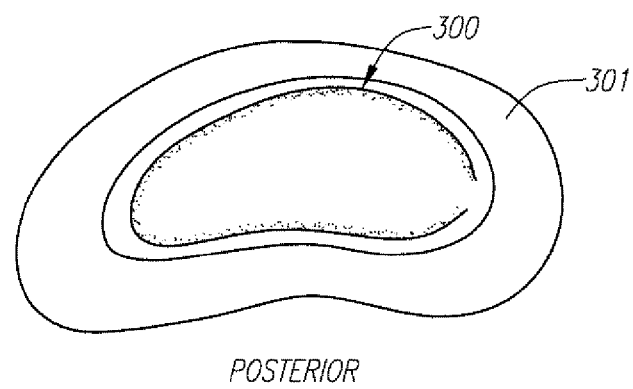
FIG. 3A is a drawing of a band according to the invention placed around the inside of the disc.
Figure 3B:
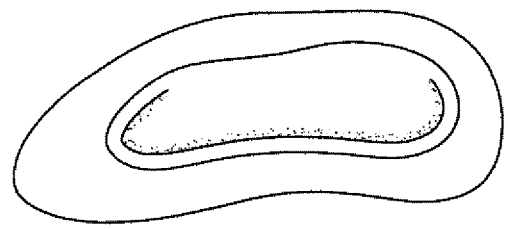
FIG. 3B is a drawing which illustrates an alternative placement of a disc band.

FIG. 3A is a drawing of a band according to the invention placed around the inside of the disc. FIG. 3B is a drawing which illustrates an alternative placement of a disc band. In the preferred embodiment, this disc bands are placed percutaneously. However, the bands may be inserted through a hole in the annulus using more traditional surgical methods, preferably the aid of an endoscope and/or endoscopic instruments.

Figure 3C:
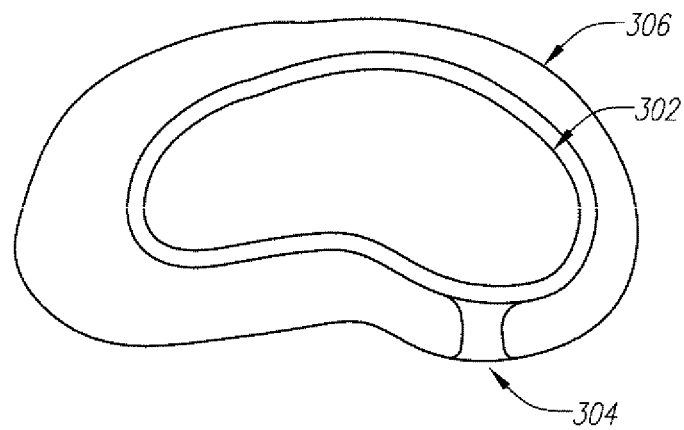
FIG. 3C illustrates the way in which a wire may be introduced through a hole in the annulus.

For example, FIG. 3C illustrates the way in which a wire 302 may be introduced through a hole 304 in the annulus 306. Once placed, the wire may serve as a guide to slide over a wider band which, in combination, would serve to block nucleus tissue from extruding through the hole. Preferably, the band would cover the entire wire or just a portion of the wire adjacent to the hole in the annulus. The wire may also be cut to facilitate insertion of the band over the wire, or the ends of the wire may be coupled after the band is placed. Multiple bands that stack upon one another may also be used with or without a wire.

Figure 3D:
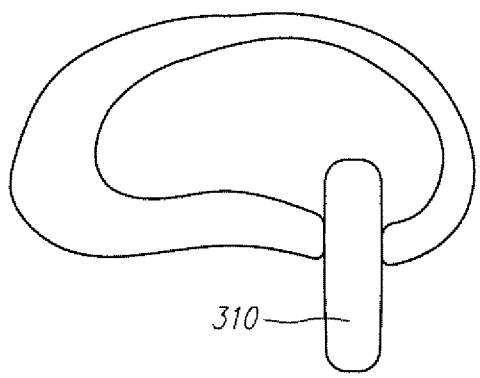
FIG. 3D is a sectional drawing which shows the introduction of a shape-memory band being inserted through a hole in the annulus.
Figure 3E:
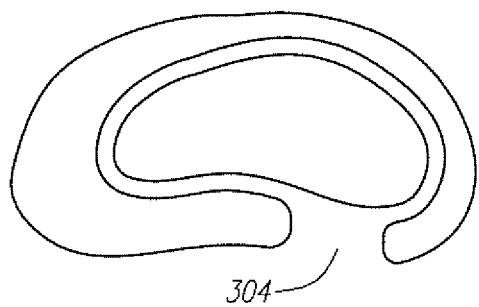
FIG. 3E is a drawing which shows the band of FIG. 3D in an expanded state operative to occlude the hole.

The wire may be of a shape-memory material, permitting insertion with a first, compressed configuration, followed by a natural expansion. Either a single wire or band may be used, or pieces may be inserted and assembled in situ. FIG. 3D is a sectional drawing which shows the introduction of a shape-memory band 310 being inserted through a hole in the annulus. FIG. 3E is a drawing which shows the band of FIG. 3D in an expanded state operative to occlude the hole 304.

Figure 3F:
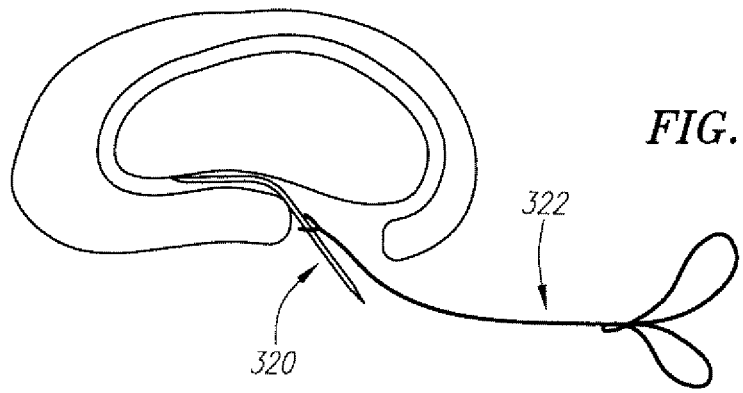
FIG. 3F is a drawing which shows the optional insertion of a band over or onto a wire of the type shown in FIGS. 3C-3E.
Figure 3G:
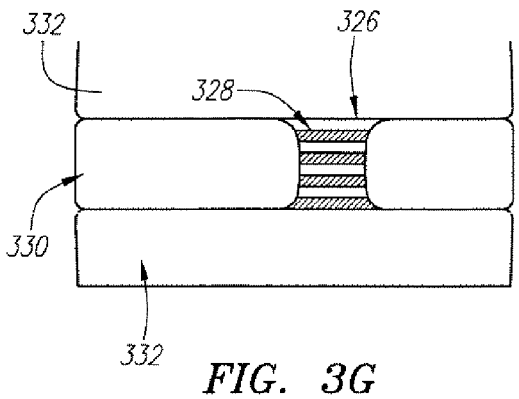
FIG. 3G is a side-view drawing illustrating how multiple wires may be used to occlude the hole in the annulus between adjacent vertebrae.
Figure 3H:
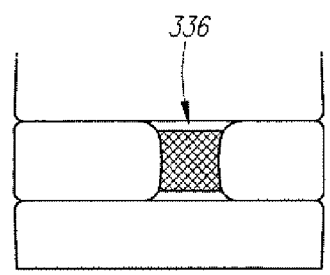
FIG. 3H illustrates the use of a single larger band placed over a wire or wires according to the present invention.

FIG. 3F is a drawing which shows the optional insertion of a band over or onto a wire of the type shown in FIGS. 3C-3E. The band is indicated at 320, with 320 referring to an instrument used to push the band along the wire or wires. FIG. 3G is a side-view drawing illustrating how multiple wires 326 may be used to occlude the hole 328 in the annulus 330 between adjacent vertebrae 332. FIG. 3H illustrates the use of a single larger band 336 placed over a wire or wires according to the invention.

Figure 3I:
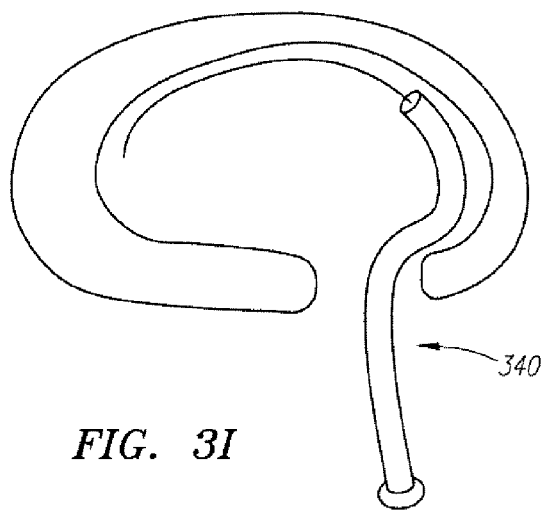
FIG. 3I shows the way in which a guide may be used to help direct bands into the disc.
Figure 3J:
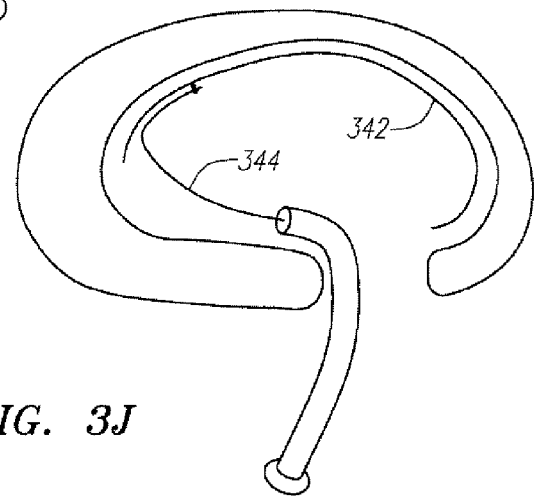
FIG. 3J shows a first band inserted into the disc, followed by a second band.
Figure 3K:
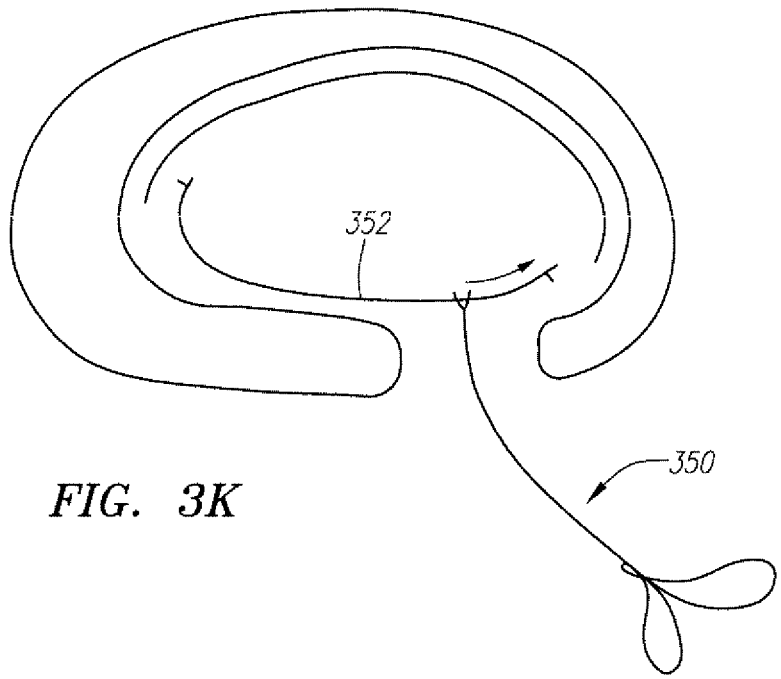
FIG. 3K illustrates the use of a separate instrument used to slide the band.
Figure 3L:
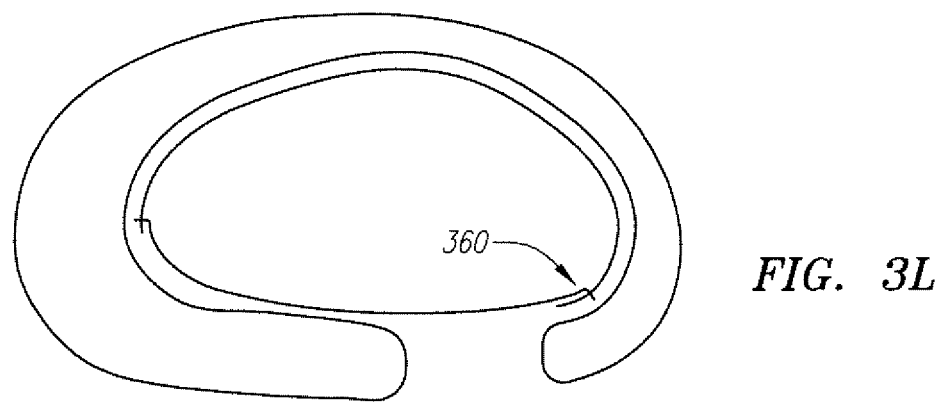
FIG. 3L is a drawing which shows how the two bands may be locked to form a complete unit to occlude a defect.
Figure 3M:
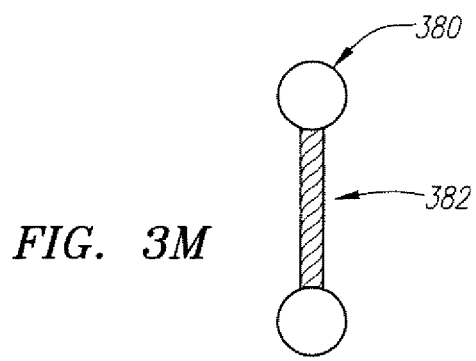
FIG. 3M is a cross-section of one embodiment of a band according to the invention.

FIG. 3I is a drawing which shows the way in which a guide 340 may be used to help direct bands into the disc. FIG. 3J, a first band 342 has been inserted into the disc, followed by a second band 344. FIG. 3K illustrates the use of a separate instrument 350 used to slide the band 352. FIG. 3L is a drawing which shows how the two bands may be locked at 360 to form a complete unit to occlude a defect. FIG. 3M is a cross-section of one embodiment of a band according to the invention, wherein a wire 380 is attached to a flexible mesh or material 382 to allow motion of the spine without impingement of the band.

Figure 4A:
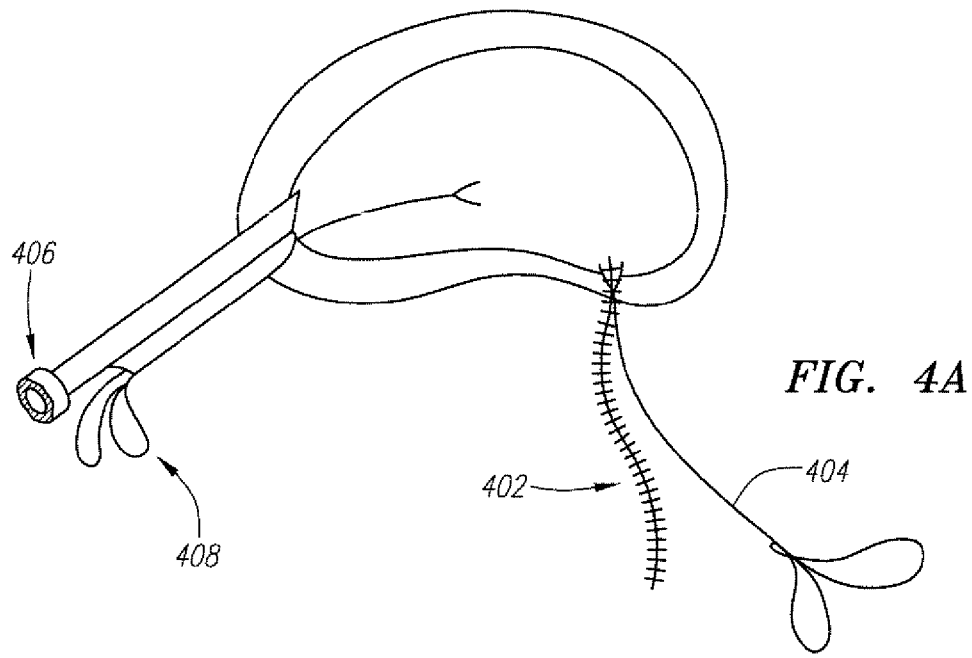
FIG. 4A begins a series of drawings which shows an endoscopic placement of bands such as those shown in FIGS. 3A and 3B.
Figure 4B:
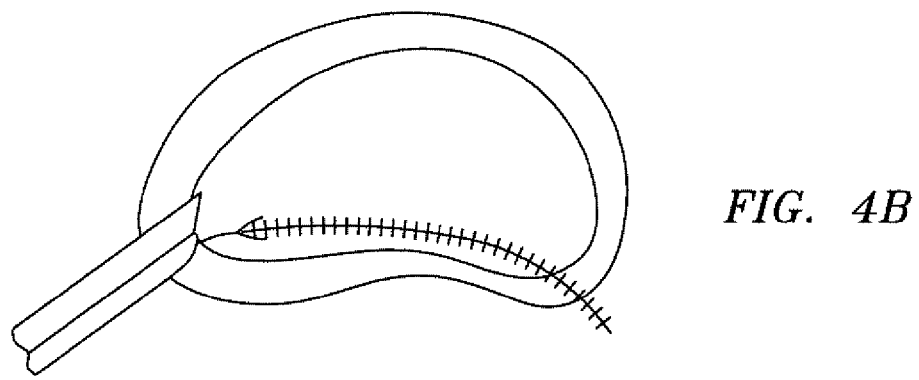
FIG. 4B shows the band entering into the annulus.
Figure 4C:
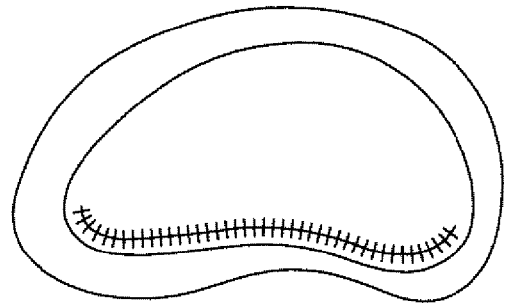
FIG. 4C shows how the band may be stapled or sutured to the inside of the annulus.
Figure 4D:
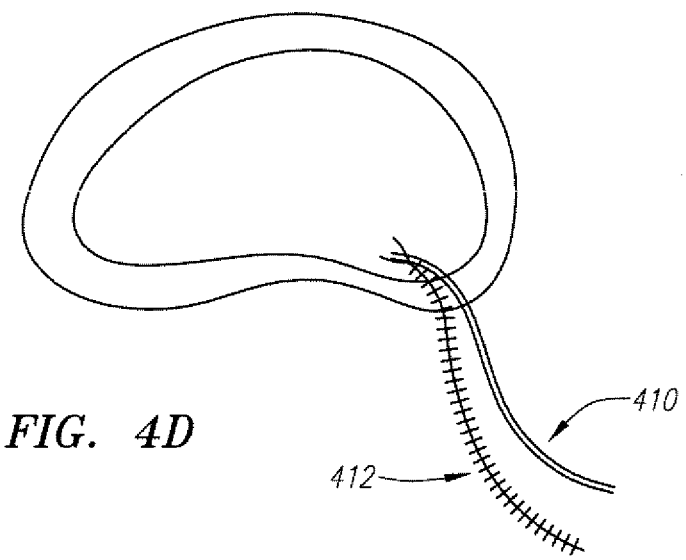
FIG. 4D illustrates the use of a steerable catheter in conjunction with an annulus band.
Figure 4E:
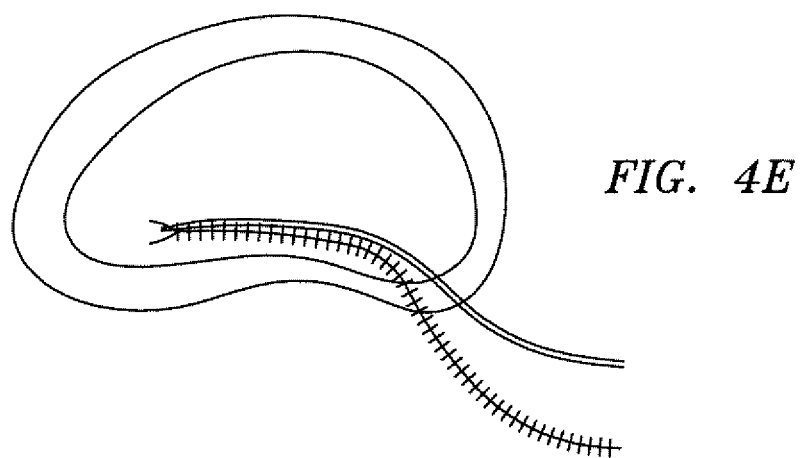
FIG. 4E illustrates a further progression of the catheter and band.
Figure 4F:
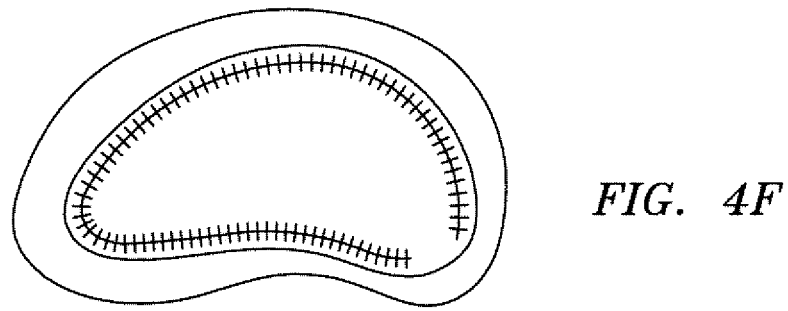
FIG. 4F shows the band in place.

FIG. 4A begins a series of drawings which shows an endoscopic placement of bands such as those shown in FIGS. 3A and 3B. FIG. 4B shows the band entering into the annulus. FIG. 4C shows how the band may be stapled or sutured to the inside of the annulus. FIG. 4D illustrates the use of a steerable catheter in conjunction with an annulus band. FIG. 4E illustrates a further progression of the catheter and band. FIG. 4F shows the band in place.

In the case of two prosthesis, two annular flaps 2002 and 2004 would preferably be created as shown in FIG. 20A. FIG. 20B is a drawing which shows the annular flaps in an open state. A prosthesis or prostheses may also be inserted through one annular flap. In addition, the prosthesis or prostheses may be inserted through the annular window that follows a procedure to remove a herniated nucleus pulpous. If annular flaps are formed, they may be sewn or sealed closed after insertion of the artificial disc or discs. The prosthetic disc or discs could restore a collapsed disc space by inflation of the prosthesis or prostheses. The vertebrae may also be distracted to restore normal disc height and aid the insertion of the prosthesis or prostheses, mechanically. As shown in FIGS. 20C-20E, a malleable band 2010 of flexible plastic, metal or other material may be inserted through the annular flaps as shown, a material with a shape memory may be beneficial for such purpose. FIG. 20C shows a situation wherein a collapsed replacement is inserted into one of the two openings, and FIG. 20D shows a disc replacement member according to the invention being inserted into the other opening. FIG. 20E shows how the band of material 2010 would be used to close both openings through suturing or other appropriate surgical techniques.

FIGS. 20F through 20H illustrate alternative approaches, wherein panels may be attached to adjacent vertebrae for the purpose of retaining disc replacement material. As shown in the front-view drawing of FIG. 20F, a flexible piece of material 2020 may be attached to adjacent vertebrae in the form of a rectangular shape or cords. Such a material would permit normal movement of the spine, and may be attached to upper and lower vertebrae through any appropriate known technique for fixation. A cloth fabric, such as Gore-Tex® or Dacron®, or a mesh screen such as nylon may be attached to the adjacent vertebrae as shown, allowing normal movement. Such a technique would be used primarily when the prosthetic disc is placed from an anterior approach to the spine, whether cervical thoracic or lumbar, and would help to restore normal annular function. As an alternative to a flexible fabric or screen, one or more retaining members 2022 may alternatively be utilized. Such a member, which may be plastic, metal or other suitable material, would be attached to one or both of the adjacent vertebrae as shown. FIG. 20G is a drawing which shows the fabric 2020 in panels 2022, as viewed from the side. FIG. 20H illustrates how materials may be applied in criss-cross fashion, in the form of bands, for example.

Mechanical distraction of the vertebra may also be used for disc replacement. U.S. Pat. No. 5,824,093, for example, describes an air jack that could be inserted through one of the flaps. Once the distraction is achieved, a prosthesis is inserted through the other annular flap. Air jacks of the type disclosed in the '093 patent may also be inserted through both annular flaps to achieve symmetric distraction. When properly distracted, one air jack may be deflated and removed. The first prosthesis would be inserted into the space formerly occupied by the air jack. After the first prosthesis is inserted, the second air jack would be deflated and removed. A second prosthesis would be inserted into the remaining disc space. A crank scissors jack could also be used to distract the vertebrae.

The intra-discal position of the prosthesis or prostheses may be maintained in a number of ways. First, the prosthesis diameter is larger in the center portion than the periphery. Second, the prosthesis expands after insertion through the annular opening. Third, the majority of annulus fibrosis is preserved. Fourth, the prosthesis exerts constant pressure on the adjacent vertebrae, securing a tight fit. Fifth, the vertebrae may be distracted so as to enlarge the disc space prior to inserting the prosthesis.

Figure 5A:
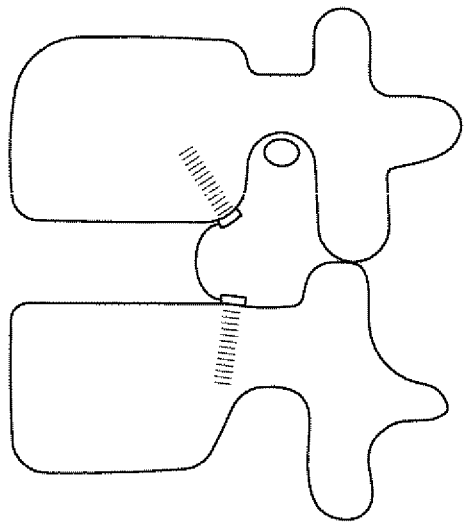
FIG. 5A is a lateral view illustrating an alternative containment device according to the invention.
Figure 5B:
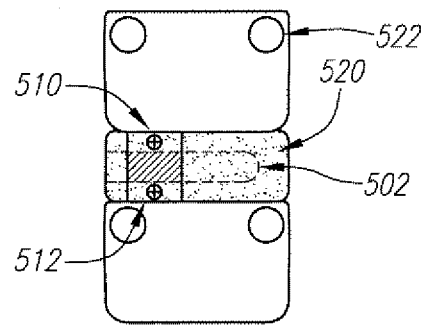
FIG. 5B is a posterior view with the lamanae and facets removed.
Figure 5C:
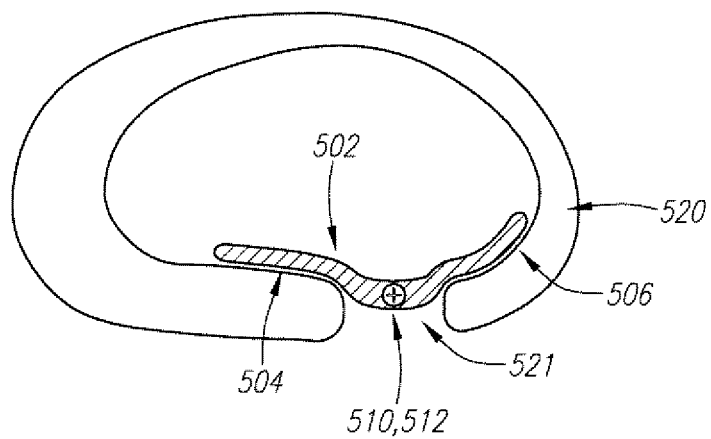
FIG. 5C is a cross-section of the device shown in FIGS. 5A and 5B.

The devices according to this invention used to retain the nucleus may also be used to contain intradiscal devices, including artificial disc replacements. The anchor members shown in particular in FIGS. 9C, 15D and 24 of U.S. patent application Ser. No. 09/807,820, for example, incorporated herein by reference, may include a mechanism that prevents the screws from backing out of the device. For example, a C-ring that snaps closed over a screw head after the head passes through the head passes through C ring may be used to prevent the screw from loosening and backing out, which could result in the compression of a nerve and the need for additional surgery. I have described various other screw back-out features, including device 410 in FIG. 4 of U.S. patent application Ser. No. 09/415,382. The preferred embodiment includes two or more screws to prevent rotation. FIG. 5A is a lateral view illustrating an alternative containment device according to the invention. FIG. 5B is a posterior view with the lamanae and facets removed. FIG. 5C is a cross-section of the device shown in FIGS. 5A and 5B. The device 502 includes lateral extensions 504 and 506 that project behind the annulus, as perhaps best seen in FIG. 5C. The device is held in place with screws 510 and 512, which are anchored to the upper and lower vertebrae, as best seen in FIG. 5A.

FIG. 6A is a detailed view of disc herniation prevention plate according to the invention. FIG. 6B is a detailed drawing of an alternative plate. Such devices may have different sizes and shapes to suit different patient physiologies. For example, the device may have asymmetric lateral extensions on the left or right side, or such extensions may be symmetric, depending upon the defect and other considerations. Such devices may be made with any suitable materials, including shape-memory materials, enabling a collapsed state of insertion, followed by an expanded state for inclusion of the defect.

The screws preferably extend through the endplate of the vertebrae, though they may also be placed into the pedicle, lamina or facet, depending upon the shape of the plate and other considerations.

The screw holes in these devices may include a C-ring to prevent backout. FIG. 7A is a drawing of a screw hole illustrating the use of a C-ring to prevent backout. FIG. 7B shows the structure of FIG. 7A with the screw progressing past the C-ring. FIG. 7C shows the screw passing through the ring, thus locking the structure in position. By way of a partial summation the retaining mechanism thus far described and the descriptions to follow preferably include a locking mechanism for the screws to prevent backout. The extension of the device extends behind the intact annulus, thereby resisting extrusion compared to devices which are entirely external, with the screws anchoring the device to prevent migration. These devices preferably collapse for entry through a hole in the annulus, then return to a desired shape to assume the blocking function. As such, the longer lateral extensions, or both extensions, may be slid behind the annulus with or without shape memory properties. In the preferred embodiments, these devices are flexible enough to allow spinal motion, that is, they are sufficiently flexible to bend and retain their normal shape with spinal flexion and extension. FIG. 8A is a drawing of a further alternative herniation prevention plate according to the invention. FIG. 8B illustrates the use of the plate 8A in position within the disc.

FIG. 9A illustrates an alternative mechanism to prevent screw backout. FIG. 9B illustrates the components of FIG. 9A from a lateral perspective, which best illustrates the use of a mobile link member 902. This mobile link member allows additional movement of the device with spinal movement while, at the same time, protects the screws from stresses that might occur through such movements. While the screws maintain the position of the device overall, the screen-like component holds the nucleus and intradiscal device in position and experiences a majority of the extrusion forces. The intact annulus adjacent to the annulus hole resists most of the extrusion force on the screen component, however.

FIGS. 10-11 illustrate the use of an alternative embodiment of the invention wherein the lateral extensions are spring-loaded as opposed to shape-memory in nature. FIG. 10A is a drawing of a plate including a spring-biased extension in an extended state. FIG. 10B illustrates the plate of FIG. 10A in a contracted state. FIG. 11A is a cut-away view of the device in the state of FIG. 10A. FIG. 11B is a cut-away view of the device of FIG. 10B, illustrating the spring being compressed.

Figure 12A:
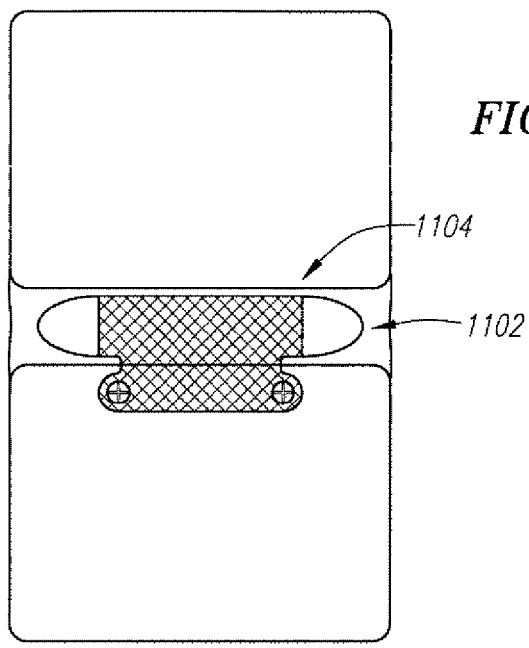
FIG. 12A illustrates a plate according to the invention incorporating an opposing pair of lateral extensions to cover the disc space more securely.
Figure 12B:
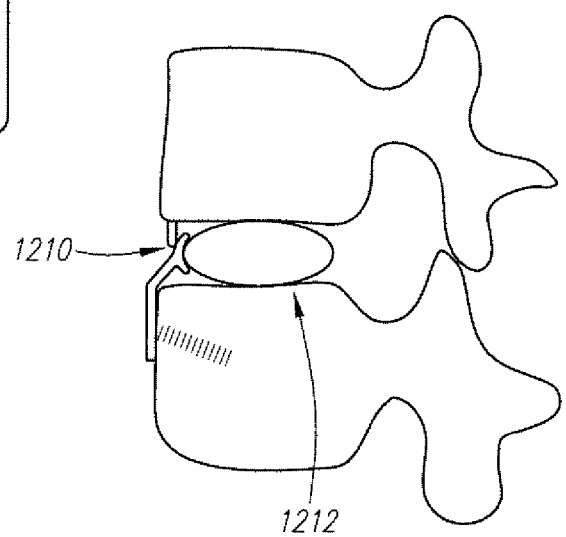
FIG. 12B is a lateral view showing the lateral extension disposed behind the patient's remaining annulus.
Figure 12C:
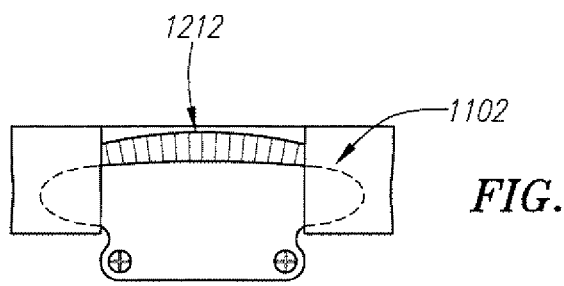
FIG. 12C is a close-up view of the device of FIGS. 12A and 12B.

FIG. 12A illustrates a plate according to the invention incorporating an opposing pair of lateral extensions to cover the disc space more securely. FIG. 12B is a lateral view showing the lateral extension disposed behind the patient's remaining annulus. FIG. 12C is a close-up view of the device of FIGS. 12A and 12B.

Figure 13A:
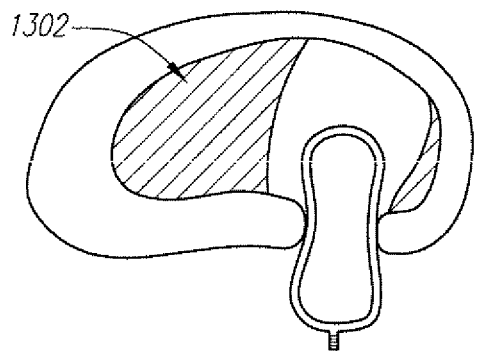
FIG. 13A begins a series of drawings illustrating an alternative embodiment according to the invention used to prevent recurrent disc herniation.
Figure 13B:
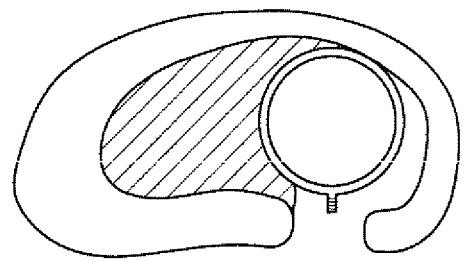
FIG. 13B illustrates the device of FIG. 13A in place within the disc space.
Figure 13C:
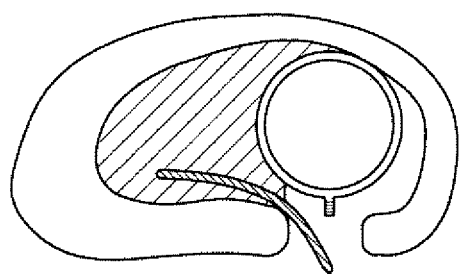
FIG. 13C illustrates the introduction of a locking member.
Figure 13D:
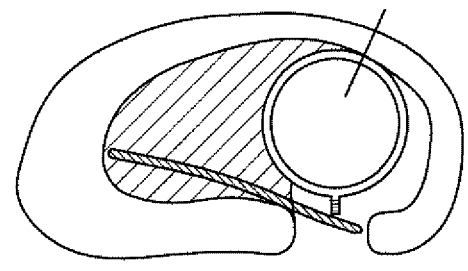
FIG. 13D shows the locking member positioned within the disc space.
Figure 13E:
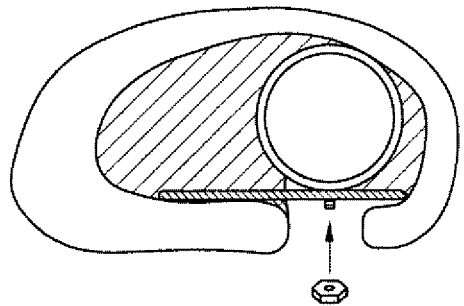
FIG. 13E shows the addition of a locking nut.
Figure 13F:
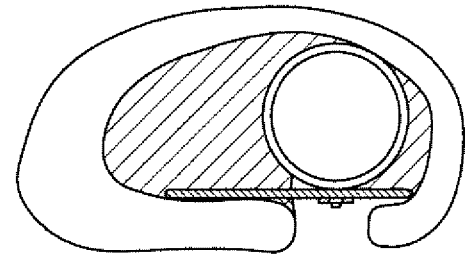
FIG. 13F shows the ring-shaped device now locked to the occluding plate.
Figure 14:
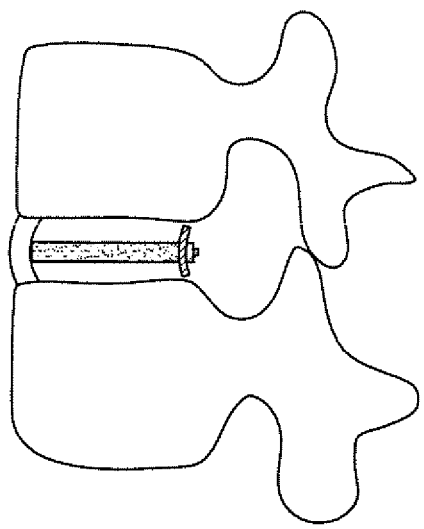
FIG. 14 shows how the devices of FIG. 13 may be provided in various sizes to suit a patient's anatomy.

FIG. 13A begins a series of drawings illustrating an alternative embodiment according to the invention used to prevent recurrent disc herniation. FIG. 13B illustrates the device of FIG. 13A in place within the disc space. FIG. 13C illustrates the introduction of a locking member. FIG. 13D shows the locking member positioned within the disc space. FIG. 13E shows the addition of a locking nut. FIG. 13F shows the ring-shaped device now locked to the occluding plate. FIG. 14 shows how the devices of FIG. 13 may be provided in various sizes to suit a patient's anatomy.

Figure 15B:
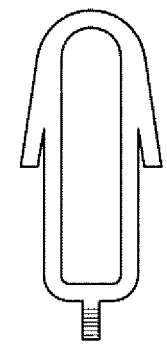
FIG. 15B shows the device of FIG. 15A in a collapsed state for insertion.
Figure 15A:
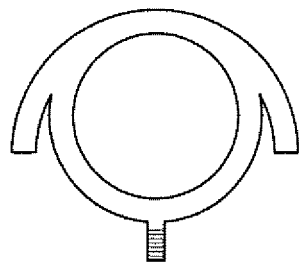
FIG. 15A illustrates yet a further embodiment of a device similar to that shown in FIGS. 13 and 14, including an anti-rotation feature.

FIGS. 15A and 15B show a further alternative embodiment of the invention making advantageous use of anti-rotation projections. FIG. 15A shows a ring-like component in an expanded state, whereas FIG. 15B shows the device collapsed for insertion. As described above with respect to other embodiments disclosed herein, such a ring-like component have a spring-like or shape-memory capability to alternate between the expanded and collapsed state. The posterior damper component also needs to be flexible enough to allow spinal extension. At the same time, however, the damper unit must retain its extended shape during flexion so as to block disc material.

Figure 16:
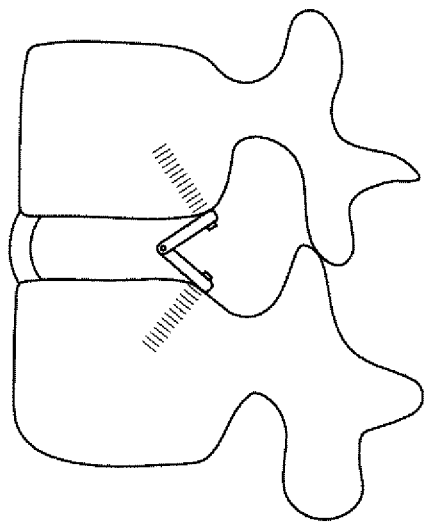
FIG. 16 is a lateral view of a different embodiment incorporating a single hinge.
Figure 17:
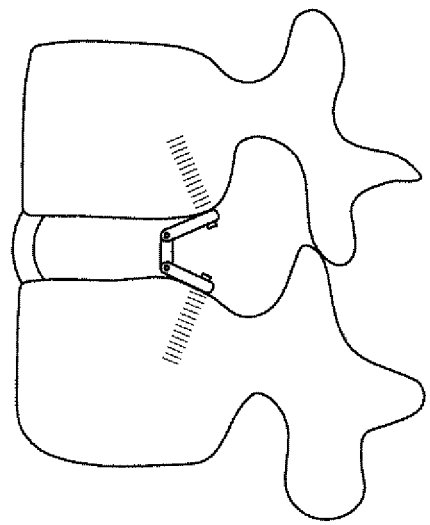
FIG. 17 is yet a different alternative embodiment of the device incorporating a plurality of hinges.
Figure 18A:
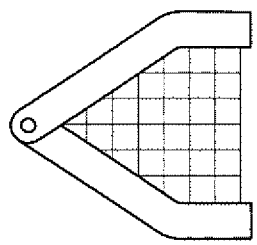
FIG. 18A shows the way in which a mesh or interdigitating teeth may be used to prevent migration of the disc material.
Figure 19A:
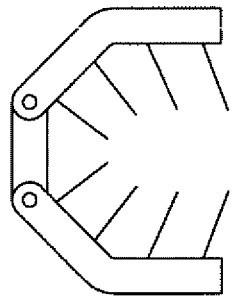
FIG. 19A shows the use of a multiple-hinge device in an extended state incorporating a mesh or interdigitating teeth.
Figure 18B:
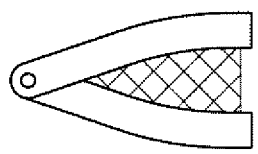
FIG. 18B shows the single-hinge device of FIG. 18A in a flexed, as opposed to extended, state.
Figure 19B:
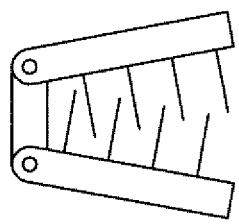
FIG. 19B shows the device of FIG. 19A in a flexed state.

FIG. 16 is a lateral view of a different embodiment incorporating a single hinge. FIG. 17 is yet a different alternative embodiment of the device incorporating a plurality of hinges. The ends of the plate may be covered with mesh, interdigitating teeth, and so forth to prevent migration of the material around the ends of the plate. FIG. 18A shows the way in which a mesh or interdigitating teeth may be used to prevent migration of the disc material. FIG. 18B shows the single-hinge device of FIG. 15A in a flexed, as opposed to extended, state. FIG. 19A shows the use of a multiple-hinge device in an extended state incorporating a mesh or interdigitating teeth. FIG. 19B shows the device of FIG. 19A in a flexed state. Preferably, the screw holes will include a mechanism to prevent backout. In addition, the component of the device that contains the screw or screws may contain a mobile link to the screen-like material. The mobile link, described above, allows additional movement of the device with spinal movement while helping to protect the screws from stresses associated with normal spinal movements.

What is claimed is:

1. A method for retaining an intra-discal material within an annulus fibrosis having a posterior annulus, an inside surface, and an opening, the opening having a lateral and a vertical dimension, comprising the steps of:

inserting a retention device through the opening in the annulus fibrosis, the retention device having length, width, and depth dimensions, the length dimension being longer than the lateral dimension of the opening in the annulus fibrosis, positioning the retention device against the posterior annulus to rest against annulus fibrosis tissues adjacent the opening on the inside surface of the annulus fibrosis, the retention device being non-hollow and being sized to rest against only a portion of the complete inside surface of the annulus fibrosis,
wherein a portion of the length dimension rests against annulus fibrosis tissues adjacent the opening to prevent the escape of intra-discal material through the opening, and wherein:
the retention device is coupled to a fixation member through the opening in the annulus fibrosis, and
the fixation member is attached to a vertebral body.

2. The method of claim 1, wherein the intra-discal material is an artificial disc.

3. The method of claim 1, wherein the opening in the annulus fibrosis is surgically formed.

4. The method of claim 1, wherein the retention device is a malleable band.

5. The method of claim 1, wherein:
the width dimension is longer than the vertical dimension of the opening in the annulus fibrosis, and
a portion of the width dimension rests against annulus fibrosis tissues adjacent the opening.

6. The method of claim 1, wherein the retention device is composed of a shape memory alloy enabling a collapsed state of insertion followed by an expanded state for preventing the escape of intra-discal material through the opening.

7. The method of claim 1, wherein the fixation member is a tab extending from the retention device.

8. The method of claim 1, wherein the retention device is coupled to the fixation member through a mobile link element.

9. The method of claim 1, wherein the fixation member is attached to a posterior portion of a vertebral body.

10. The method of claim 1, wherein the fixation member is attached to a posterior surface of a vertebral body.

11. The method of claim 1, wherein the fixation member is attached to upper and lower vertebral bodies.

12. The method of claim 1, wherein the fixation member is attached with one or more screws.

13. The method of claim 1, wherein the fixation member is attached with one or more screws through the endplate of a vertebral body.

14. The method of claim 1, wherein the fixation member is attached with one or more pedicle screws.

15. The method of claim 1, wherein the fixation member is attached with one or more laminar screws.

16. The method of claim 1, wherein the fixation member is attached with one or more facet screws.

17. A device for retaining intra-discal material within an annulus fibrosis having a posterior annulus, an inside surface, and an opening, the opening having a lateral and a vertical dimension, comprising:
a retention device having length, width, and depth dimensions, the length dimension being longer than the lateral dimension of the opening in the annulus fibrosis such that a portion of the length dimension rests against annulus fibrosis tissues adjacent the opening to prevent the escape of intra-discal material through the opening, the retention device being non-hollow and being sized to rest against only a portion of the complete inside surface of the annulus fibrosis;
a fixation member coupled to the retention device through the opening in the annulus fibrosis; and
a fastener for attaching the fixation member to a vertebral body.

18. The device of claim 17, wherein the intra-discal material is an artificial disc.

19. The device of claim 17, wherein the retention device is a malleable band.

20. The device of claim 17, wherein:
the width dimension of the retention device is longer than the vertical dimension of the opening in the annulus fibrosis, and
a portion of the width dimension rests against annulus fibrosis tissues adjacent the opening.

21. The device of claim 17, wherein the retention device is composed of a shape memory alloy enabling a collapsed state of insertion followed by an expanded state for preventing the escape of intra-discal material through the opening.

22. The device of claim 17, wherein the fixation member is a tab extending from the retention device.

23. The device of claim 17, wherein the retention device is coupled to the fixation member through a mobile link element.

24. The device of claim 17, wherein the fastener is a bone screw.

25. The device of claim 17, wherein the fastener is a screw extending through the endplate of a vertebral body.

26. The device of claim 17, wherein the fastener is a pedicle screw.

27. The device of claim 17, wherein the fastener is a laminar screw.

28. The device of claim 17, wherein the fastener is a facet screw.

* * * * *